(12) United States Patent
Glossop (10) Patent No.: US 6,203,543 B1
(45) Date of Patent: Mar. 20, 2001

(54) DEVICE FOR RELEASABLY SECURING OBJECTS TO BONES

(76) Inventor: Neil David Glossop, 6 Cactus Avenue, Toronto (CA), M2R 2T5

( * ) Notice: Subject to any disclaimer, the term of this patent is extended or adjusted under 35 U.S.C. 154(b) by 0 days.

(21) Appl. No.: 09/336,691

(22) Filed: Jun. 21, 1999

(51) Int. Cl.$^7$ .................................................. A61B 17/56
(52) U.S. Cl. .............................. 606/60; 606/61; 606/62; 606/73
(58) Field of Search .................................. 606/66, 61, 73, 606/60, 62, 29, 53, 54, 57, 59; 411/403, 187, 389, 200, 383, 537

(56) References Cited

U.S. PATENT DOCUMENTS

| 5,487,744 | 1/1996 | Howland . | |
|---|---|---|---|
| 5,545,228 | 8/1996 | Kambin . | |
| 5,728,127 | * 3/1998 | Asher et al. ............................ | 606/61 |
| 5,741,255 | * 4/1998 | Krag et al. .............................. | 606/61 |
| 5,810,814 | 9/1998 | Newson . | |

* cited by examiner

Primary Examiner—Michael Buiz
Assistant Examiner—Anthony S. King
(74) Attorney, Agent, or Firm—Riches, McKenzie & Herbert LLP; Jeffrey Pervanas (57) ABSTRACT

A device to releasably secure an object to a bone is disclosed. The device has a rotation restricting member which, while engaging the bone, prevents rotation of the member. The device also comprises an axial supporting member which axially secures the device to the bone, and preferably comprises a bone screw. While the bone screw and rotation restricting member engage the bone, a fastening mechanism fastens the rotation restricting member to the bone screw. In this way, objects can be releasably secured to the rotation restricting member or the bone screw by means of a clamp to temporarily axially and rotationally secure the objects to the bone. Preferably, the rotation restricting member comprises a sleeve and the fastening mechanism comprises a nut which engages threads on the bone screw. The sleeve comprises serrated teeth which, when biased towards the bone, engage the bone to restrict rotation of the sleeve. Rotation of the nut about the threads on the bone screw axially bias the sleeve towards the bone such that the serrated teeth engage the bone to restrict rotation of the sleeve about the screw and to fasten the sleeve to the bone screw.

21 Claims, 8 Drawing Sheets

DEVICE FOR RELEASABLY SECURING OBJECTS TO BONES

FIELD OF THE INVENTION

This invention relates to devices for securing objects to bones. More particularly, this invention relates to devices which releasably secure objects to bones such that the object is temporarily axially and rotationally secured to the bone.

BACKGROUND OF THE INVENTION

Various types of surgical procedures now require objects, such as tools or tracking devices, to be temporarily secured to a bone during a procedure. For example, during image guided surgery, it is sometimes necessary to attach active or passive trackers to bones in order to determine the location of a bone with respect to the image. This is required, for instance, for alignment procedures, such as fracture reductions. It is also often necessary to attach active or passive dynamic reference objects to bones. In addition, it is sometimes necessary to temporarily attach objects to bones, such as drill guides or templates to perform a subsequent drilling or sawing operation.

Furthermore, it is sometimes necessary to secure objects to the bone which must remain temporarily secured after the initial surgical procedure. For example, external fixation devices are sometimes secured to bones or bone fragments to hold the bone and bone fragments in place during healing. Also, spinal rods must sometimes be secured to vertebrae, thereby temporarily mechanically immobilizing areas of the spine, to treat certain types of spinal column disorders. Also, to analyze and treat certain joint pathologies, it is sometimes necessary to attach trackers to bones to measure the discrete joint movements, such as, for example, to measure the motion patterns of the human knee.

It has been known in the past to use bone screws to secure objects to bones. Bone screws generally have a coarse thread at one end for engaging the bone and a means at the other end to easily attach clamps or instruments thereto. While bone screws have worked well in the past, they are susceptible to rotational displacement which can either loosen or tighten the bone screw. This rotational displacement can be caused in different ways, such as by the normal cyclical force applied to the bone screw or through inadvertent contact with the object attached to the bone screw by an external source.

It is clear that rotational displacement of the bone screw will affect the object secured to the bone screw. For example, any rotational displacement of the bone screw may cause a rotational displacement of the object with respect to the bone. Furthermore, any rotational displacement of the bone screw may cause an axial displacement of the bone screw along the axis of rotation of the bone screw with respect to the bone. It is clear that any axial and/or rotational displacement of the bone screw with respect to the bone will also cause an axial and/or rotational displacement of the object with respect to the bone.

In some cases, any rotational or axial displacement of the screw can have a significant effect on the procedure. For example, during image guided surgery, the objects, such as tracking devices or instruments, secured to the bone screw will be registered in six degrees of freedom, namely three displacement degrees of freedom and three rotational degrees of freedom. Accordingly, any axial or rotational displacement of the bone screw will cause an axial or rotational displacement of the object and require re-registration of the object secured to the bone screw.

In the past, in order to avoid rotational displacement of the bone screw, and therefore rotational or axial displacement of objects attached to bone screws, more than one bone screw has been used to attach an object to a bone. For example, two or more bone screws, displaced along the bone, have been used to prevent detrimental effects caused by rotational displacement of one bone screw. However, using additional bone screws weakens the bones being treated and increases the length of time of the procedure. In addition, in some cases, it is not practical to use several bone screws because the bones or bone fragments are simply not large enough. Also, use of several bone screws restricts access to the operative site, which can be the case with the vertebrae of the spine.

Accordingly, there is a need in the art for a device which prevents rotational displacement of bone screws. In addition, there is a need in the art for a device which better axially and rotationally secures objects to bones.

SUMMARY OF THE INVENTION

Accordingly, it is an object of this invention to at least partially overcome the disadvantages of the prior art. Also, it is an object of this invention to provide an improved type of device which can better axially and rotationally secure objects to bones.

Accordingly, in one of its aspects, the present invention resides in a device for releasably securing an object to a bone, said device comprising: a rotation restricting member having an engaging element which engages the bone to restrict rotation of the member; a fastening mechanism for fastening the rotation restricting member to a bone screw engaging the bone; a clamp for releasably securing the object to the rotation restricting member or the bone screw; wherein after the fastening mechanism has fastened the rotation restricting member to the bone screw, the rotation restricting element is biased towards the bone such that the engaging element engages the bone to restrict rotation of the member; and wherein releasably securing the object to the clamp axially and rotationally secures the object to the bone.

In a further aspect, the present invention resides in a device for releasably securing an object to a bone, said device comprising: a clamp releasably securable to the object; an axial supporting member for axially securing the device to the bone; a rotation restricting member which, while engaging the bone, restricts rotation of the device; a fastening mechanism for fastening the axial supporting member with respect to the rotation restricting member; wherein the fastening mechanism fastens the axial supporting member to the rotation restricting member while the axial supporting member and the rotation restricting member are engaging the bone; and wherein objects can be releasably secured to the clamp, after the fastening mechanism has fastened the axial supporting member with respect to the rotational supporting member, to axially and rotationally secure the objects to the bone.

In a still further aspect, the present invention resides in a device to restrict rotational displacement of a bone screw, said device comprising: a rotation restricting member having an engaging element which engages the bone to restrict rotation of the rotation restricting member; a fastening mechanism for fastening the rotation restricting member to the bone screw; wherein the fastening mechanism fastens the rotation restricting member to the bone screw while the engaging element is engaging the bone, thereby preventing rotational displacement of the bone screw.

In a still further aspect, the present invention resides in a device for releasably securing an object to a bone, said device comprising: a rotation restricting member having an engaging element which engages the bone to restrict rotation of the member; a bone screw for engaging the bone; a biasing member for axially biasing the rotation restricting element with respect to the bone screw; wherein after the bone screw has engaged the bone, the biasing member axially biases the rotation restricting member with respect the bone screw such that the engaging element engages the bone to restrict rotation of the member; and wherein releasably securing the object to the rotation restricting member axially and rotationally secures the object to the bone.

In a further aspect, the present invention provides a method of releasably securing an object to a bone, said method comprising the steps of: fixing a biasing member to a longitudinal position on a bone screw, said bone screw having a bone engaging end; axially inserting a rotation restricting member onto the bone engaging end of the bone screw, said rotation restricting member having an engaging element which engages the bone to restrict rotation of the rotation restricting member; driving the bone engaging element of the bone screw into the bone until the biasing member biases the engaging element of the rotation restricting member into the bone; clamping the object to the rotation restricting element or the bone screw.

Accordingly, one advantage of the present invention is that an object, such as a tracker or surgical tool, can be better secured, both rotationally and axially, to bones. A further advantage of the present invention is that rotation of the bone screw is restricted, thereby avoiding rotational displacement of the bone screw. A further advantage of the device to restrict rotation of the bone screw is that the device is located near the bone screw and fastened to the bone screw such that the device has a small "footprint" and does not require a large space on the bone. This allows the device according to the present invention to be more easily used in a surgical setting, and, prevents the need for several bone screws to be inserted into a single bone.

A further advantage of the present invention is that, because the device requires a small footprint, the present invention can be used in relatively small bones, such as the vertebrae which form the spinal column and on fragments of bones. The present invention also does not overly obstruct the operative site. Furthermore, even in larger bones where two or more bone screws can be inserted to better rotationally secure an object to the bone, it is often not desirable to use more bone screws because additional bone screws require more time to insert and remove, and, further weaken the bone.

A further advantage of the present invention is that the rotation restricting member will generally engage only the surface of the bone, and will not threadably engage a bone, such as in a manner that a bone screw does. Accordingly, a further advantage of the present invention is that the device according to the present invention rotationally and axially secures an object to the bone in a relatively non-intrusive manner, especially as compared with using two or more bone screws.

A still further advantage of the present invention is that the rotation restrictive member can take several different forms in different embodiments. This permits different fastening mechanisms to be used. Also, this provides a further advantage in that specific types of fastening mechanisms can be used in different situations to best axially and rotationally secure an object to a bone for each type of situation.

A still further advantage of the present invention is that the biasing member can be fixed to a specific longitudinal position on the bone screw. In this way, the bone screw can be inserted a predetermined distance into the bone before the biasing member biases the engaging element of the rotation restricting member into the bone. This ensures that the bone screw will not be inserted into the bone beyond a predetermined depth.

Further aspects of the invention will become apparent upon reading the following detailed description and drawings which illustrate the invention and preferred embodiments of the invention.

BRIEF DESCRIPTION OF THE DRAWINGS

In the drawings, which illustrate embodiments of the invention:

FIG. 3C shows a front view and

DETAILED DESCRIPTION OF THE PREFERRED EMBODIMENTS

Figure 1:
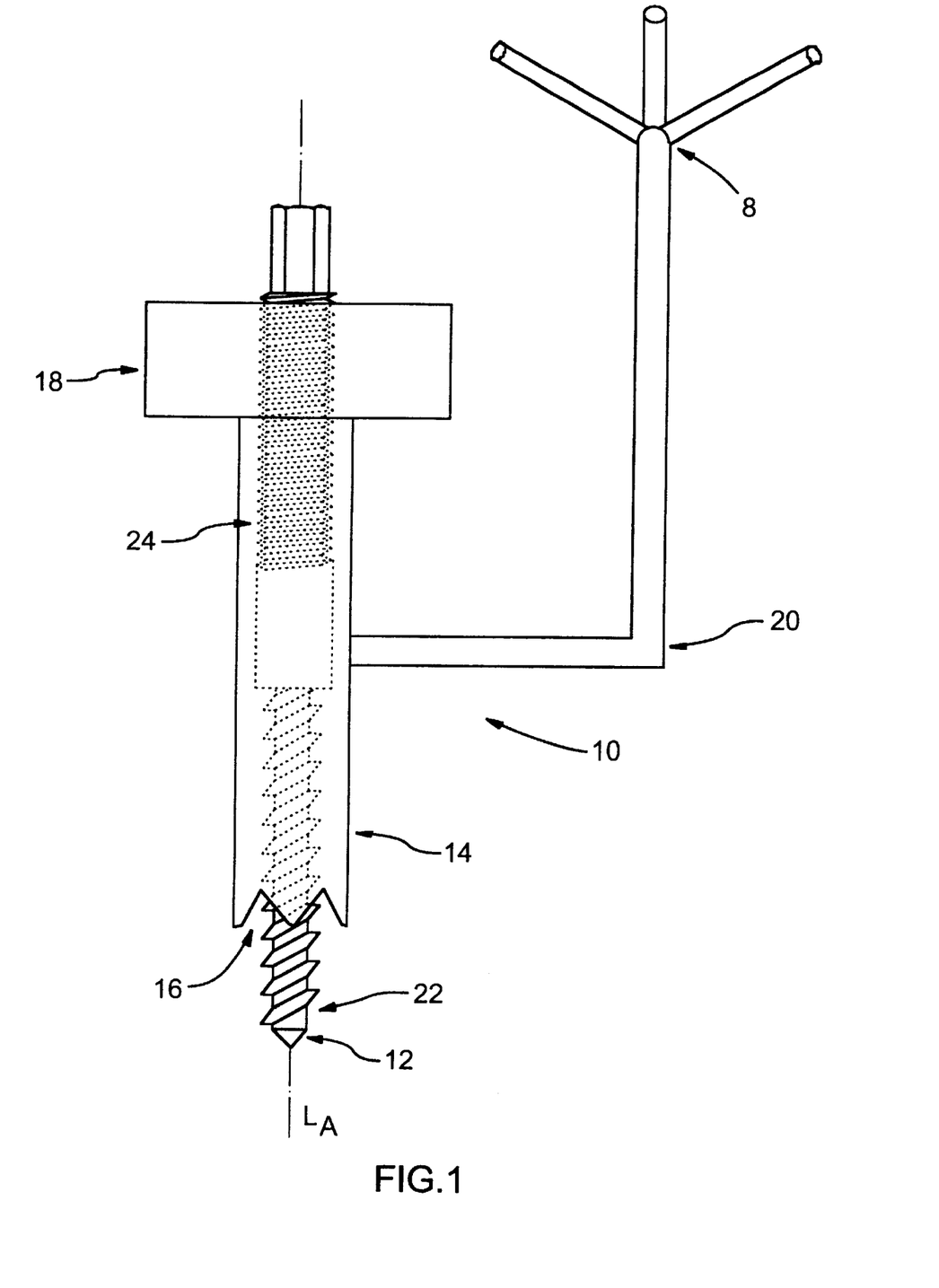
FIG. 1 is a schematic diagram of one embodiment of the present invention utilizing a sleeve.

As shown in FIG. 1, one embodiment of the present invention provides a device, shown generally by reference numeral 10, for temporarily axially and rotationally securing objects 8 to a bone. As shown in FIG. 1, the device 10 comprises a sleeve 14 having serrated teeth 16 for engaging the bone 6. A fastening mechanism, shown generally in FIG. 1 by nut 18, is used to bias the sleeve 14 against the bone such that the serrated teeth 16 engage the bone 6. While the sleeve 14 is biased towards the bone 6, the serrated teeth 16 are biased into engagement with the bone 6, thereby fastening the sleeve 14 to the bone 6. Thus the nut 18 acts as a biasing member to bias the sleeve 14 towards the bone 6 and to thereby fasten the sleeve 14 to the bone screw 12 and to also fasten the sleeve 14 to the bone 6.

Bone screws, such as bone screw 12 shown in FIG. 1, are generally well known in the art. As shown in FIG. 1, the bone screw 12 includes a first threaded end 22 which generally has a coarse thread for anchoring the bone screw 12 in the bone. While the first threaded end 22 of the bone screw 12 can be inserted directly into and engage the bone 6, it is sometimes useful to have a hole drilled or drilled and tapped in the bone 6 to guide the bone screw 12. The bone screw 12 also may have a second end 24, opposite the first threaded end 22. The second end 24 may be threaded, as shown in FIG. 1, or have other means that can be used to fasten elements to the bone screw 12.

The device 10 further comprises a clamp 20 for releasably securing the object 8 to the sleeve 14 or bone screw 12. The clamp 20 is shown generally in the figures, and, it is understood that any type of clamp which can secure the object 8 to the sleeve 14 or the bone screw 12 can be used.

Preferably, the clamp 20 releasably secures the object 8 to the sleeve 14 because the sleeve 14 is less susceptible to rotational displacement by inadvertent contact with the object 8. However, once it is fastened to the bone screw 12, the sleeve 14 restricts rotation of the bone screw 12 such that the clamp 20 could releasably secure the object 8 to the bone screw 12 also. In the case of the embodiment shown in FIG. 1, the bone screw 12 will not move much because of friction between the nut 18 and sleeve 14 and between the nut 18 and bone screw 12. To increase this friction, it is further preferred for the threads on the first threaded end 22 to differ from the threads of the second threaded end 24 thereby further restricting rotation of the sleeve 14 and bone screw 12 about the longitudinal axis $L_A$.

The object 8 shown in FIG. 1 is a representation of a tracking device, such as the tracking device disclosed in U.S. Pat. No. 5,834,759. The tracking device could be used, for instance, to track the location of the bone 6 during image guided surgery. It is understood that even though a tracking device is shown as being the object 8 which the clamp 20 releasably secures to the sleeve 14, any type of object 8 could be used. In addition, it is understood that in some cases, the object 8 may comprise a clamp 20 such that the object 8 could be directly clamped to the sleeve 14.

Figure 2A:
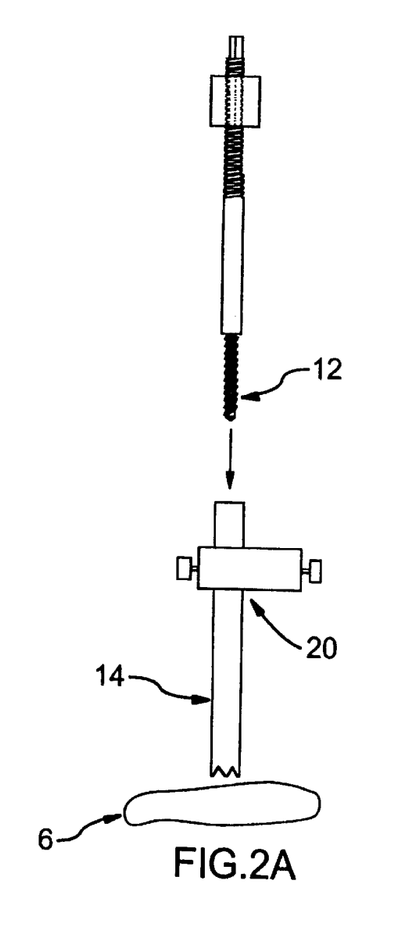
FIGS. 2A, 2B, 2C and 2D illustrate insertion of the device shown in FIG. 1 into a bone.
Figure 2B:
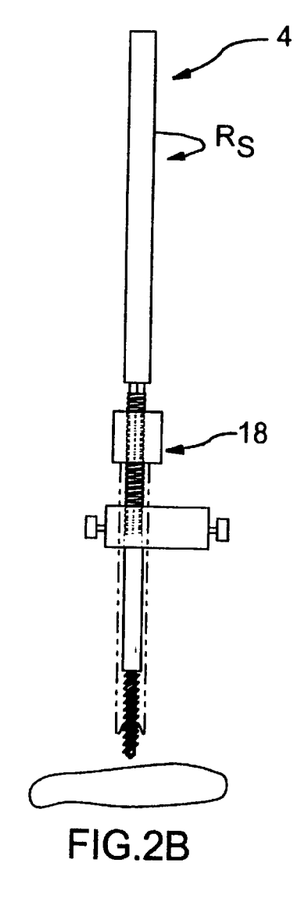

FIGS. 2A, 2B, 2C and 2D show the device 10 being inserted into a bone 6. As shown in FIG. 2A, the sleeve 14 axially receives the bone screw 12. As also shown in FIG. 2A, the clamp 20 is secured to the sleeve 14 at this step, but could also be secured at a later step. As shown in FIG. 2B, a screw driver shaft 4 is used to screw the bone screw 12 into the bone 6 by rotating the bone screw 12 in the direction $R_S$ about the longitudinal axis $L_A$. It is apparent that rotationally displacing the bone screw 12 the direction $R_S$ will cause the bone screw 12 to become axially displaced along the longitudinal axis $L_A$. Depending on the situation, a pilot hole (not shown) could be drilled or drilled and tapped to assist in rotating the screw driver shaft 4 and driving the bone screw 12 into the proper location.

Figure 2C:
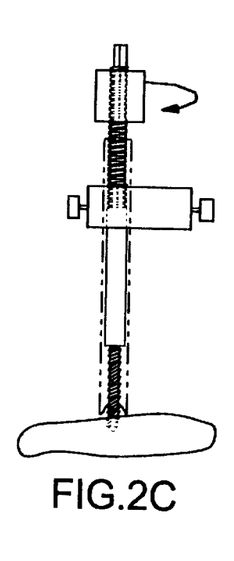

In FIG. 2C, the bone screw 12 has engaged the bone 6 and has been screwed to the proper depth. At this time, the nut 18 can be rotated about the threads 24. Rotation of the nut 18 about the threads on the second threaded end 24 axially biases the sleeve 14 towards the bone 6 and biases the serrated teeth 16 into engagement with the bone 6. In this way, the sleeve 14 is fastened to the bone screw 12 and the serrated teeth 16 engage the surface of the bone 6 to restrict rotation of the sleeve 14 about the longitudinal axis $L_A$ of the device 10.

Figure 2D:
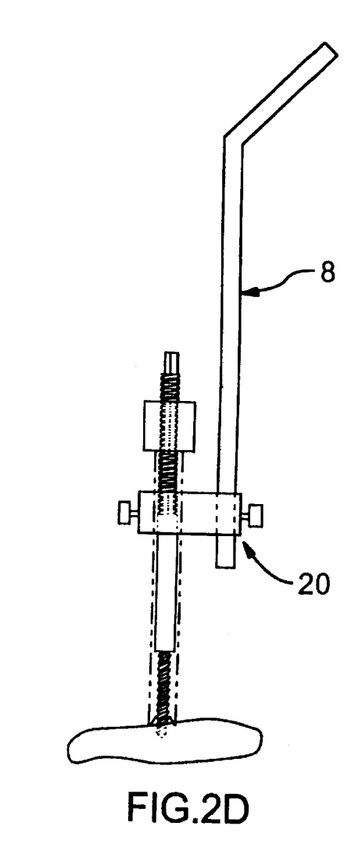

In FIG. 2D, the device 10 is shown with the sleeve 14 and serrated teeth 16 biased towards the bone 6, and, the nut 18 having fastened the sleeve 14 to the bone screw 12. At this time, the object 8 can be releasably secured to the device 10 by means of the clamp 20. Releasably securing the object 8 to the device 10 will axially and rotationally secure the object 8 to the bone 6.

Figure 3A:
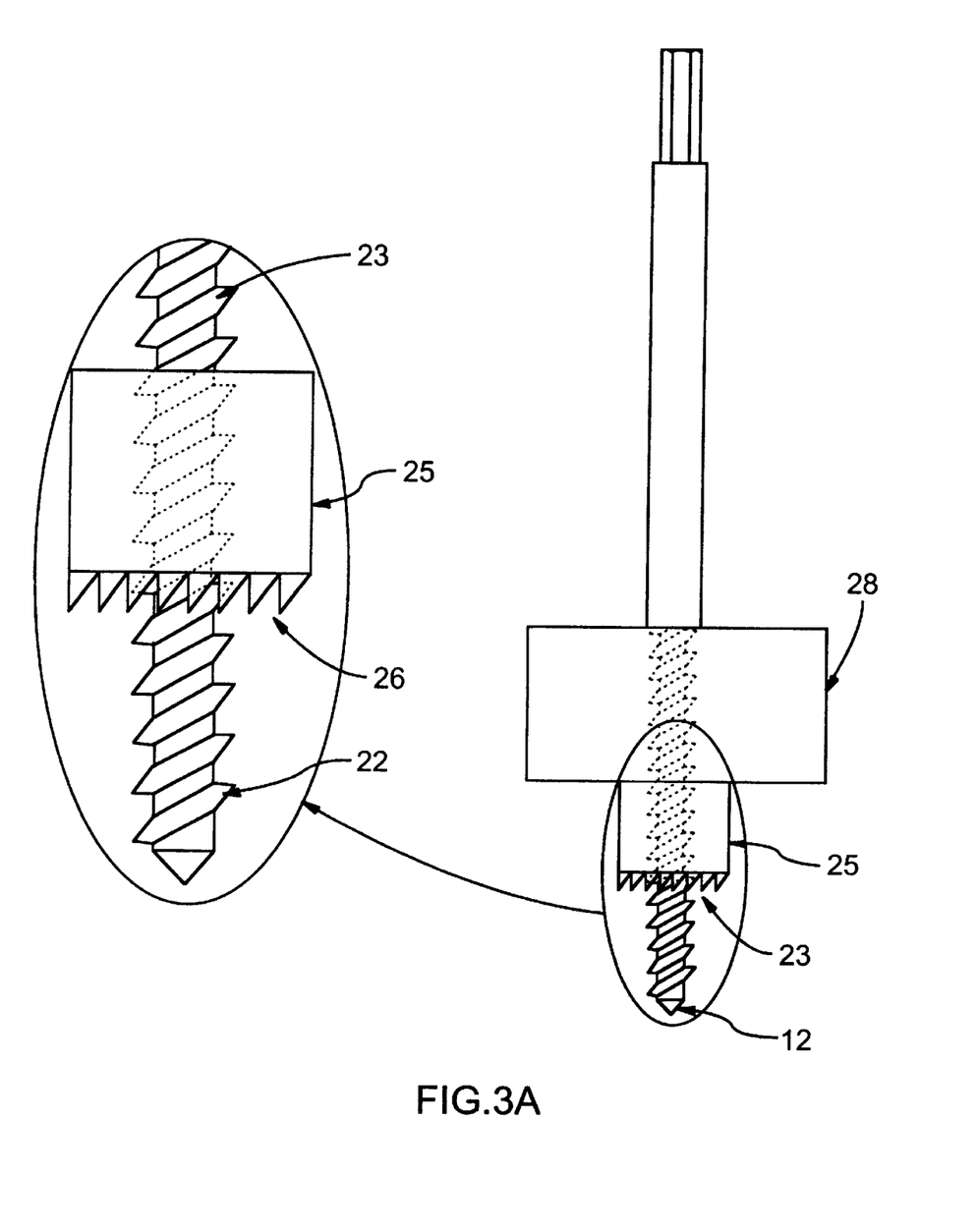
FIG. 3A shows a further embodiment of the present invention utilizing a washer having serrated teeth.

FIG. 3A shows a further embodiment of the present invention. As shown in FIG. 3A, rather than having a sleeve 14 as the rotation restricting member, a washer 25 is shown as the rotation restricting member. The washer 25 has an opening 23 which axially receives the bone screw 12. As shown in FIG. 3A, the opening 23 receives the first threaded end of the bone screw 12, which are generally the coarse threads 22 to engage the bone 6. The washer 25 also has serrated teeth 26 which act as the engaging element to engage the surface of the bone 6. In this embodiment, a nut 28, which engages the threads 22, acts as the fastening mechanism and biasing member to axially bias the washer 25 towards the bone 6, thereby biasing the serrated teeth 26 into engagement with the bone 6 and fastening the washer 25 to the bone screw 12 and fastening the washer 25 to the bone 6. The clamp 20 could then be attached to the washer 25.

Figure 3B:
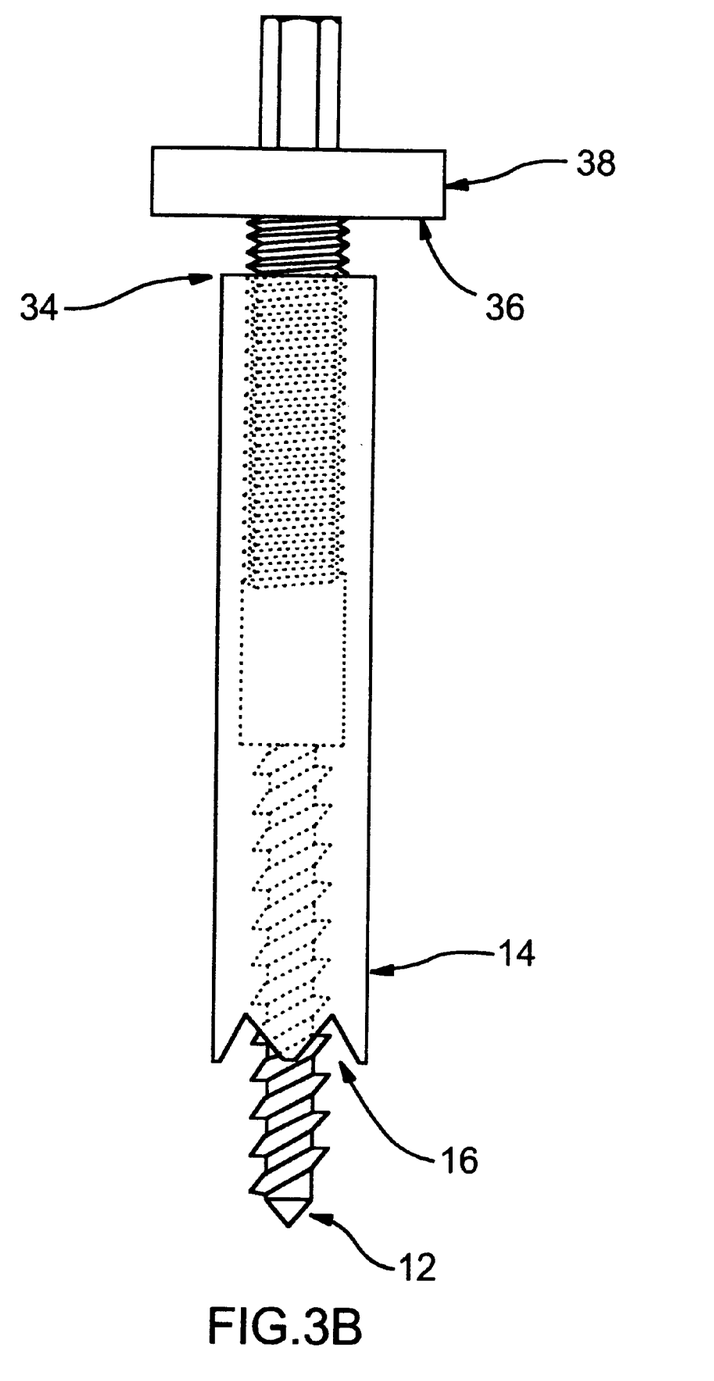
FIG. 3B shows a further embodiment of the present invention utilizing a retainer as the fastening mechanism.

FIG. 3B shows a further embodiment of the present invention where a retainer 38 is fixed to the bone screw 12. The retainer 38 has a stop 36 which engages a portion 34 of the sleeve 14. The sleeve 14 in the embodiment shown in FIG. 3B is similar to the sleeve 14 shown in FIG. 1.

As the bone screw 12 is inserted into a bone 6, the stop 36 of the retainer 38 will engage the portion 34 of the sleeve 14, thereby axially biasing the sleeve 14 towards the bone 6 and bringing the serrated teeth 16 into engagement with the surface of the bone 6. This embodiment shown in FIG. 3B may be used where the bone screw 12 must be inserted to a particular depth before the sleeve 14 restricts further rotation of the bone screw 12. This embodiment could be advantageous where a surgeon does not desire the bone screw 12 to be inserted past the predetermined depth in the bone 6 and can control the predetermined depth by fixing the retainer 38 to a desired longitudinal position along the longitudinal axis $L_A$ of the bone screw 12.

In a preferred embodiment, the retainer 38 is axially adjustable so that the predetermined depth the bone screw 12 may be inserted is set by the surgeon before the procedure is commenced. The retainer 38 could be axially adjusted, for example, by having the retainer 38 threadably engage the bone screw 12. In addition, if the retainer 38 is fixed to the bone screw 12, washers or other elements can be placed between the stop 36 and the portion 34 of the sleeve 14 to effectively lower the longitudinal position at which the stop 36 will engage the portion 34 of the sleeve 14.

If desired, the other embodiments of the invention may also be adapted to be used to insert the bone screw 12 to a particular depth before the sleeve 14 restricts further rotation of the bone screw 12. For example, with respect to the embodiment illustrated in FIG. 1, the nut 18 could be rotated to a longitudinal position on the bone screw 12 and then the bone screw 12 could be inserted into the bone 6 a predetermined distance until the sleeve engages the nut 18. In the embodiment shown in FIG. 1, however, the nut 18 may rotate slightly as the bone screw 12 is rotated by the screw driver shaft 4. To prevent this rotation, a thumb screw (not shown) could be inserted into a perpendicularly threaded hole (not shown) in the nut 18. The thumb screw (not shown) would be preferably made from plastic and would engage the bone screw 12 to prevent rotation of the nut 18 and movement of the nut 18 from the longitudinal position.

Figure 3C:
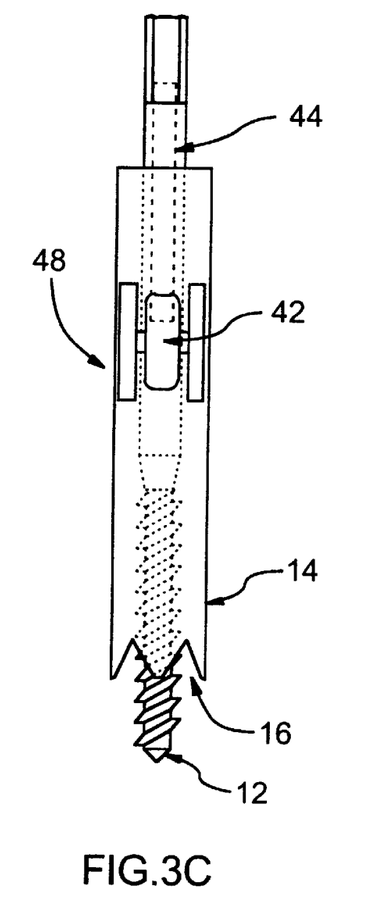
Figure 3D:
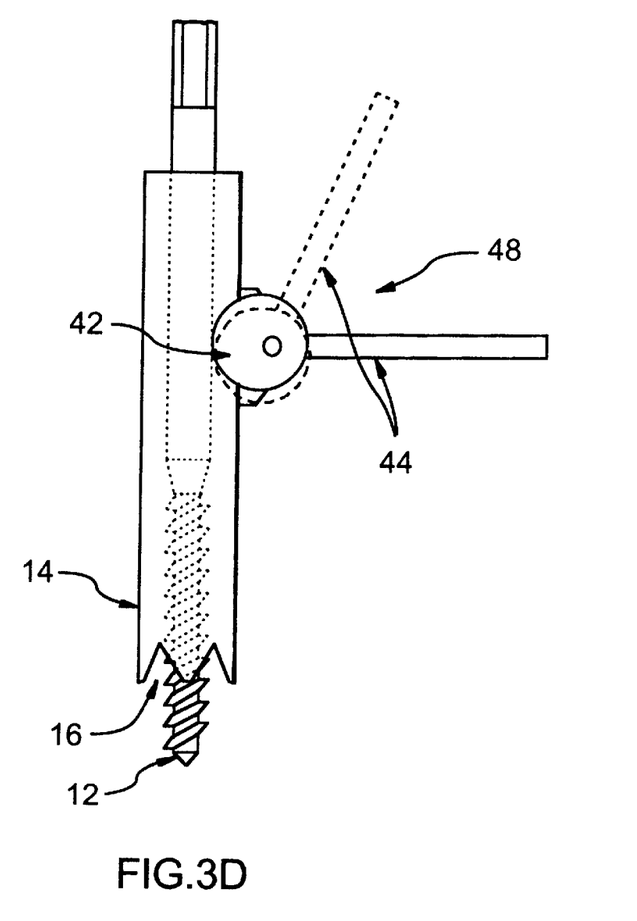
FIG. 3D shows a side view, respectively, of an embodiment of the present invention utilizing a further type of fastening mechanism having an eccentrically mounted disc.

FIGS. 3C and 3D show a front view and side view, respectively, of a further embodiment of the present invention. The sleeve 14 shown in FIGS. 3C and 3D is similar to the sleeve 14 shown in FIG. 1. However, the sleeve 14 shown in FIGS. 3C and 3D comprises a cam or eccentrically mounted disc 42 connected to a locking lever 44. The eccentrically mounted disc 42 and locking lever 44 together act as a locking mechanism, shown generally by reference numeral 48.

The fastening mechanism 48 will also generally rotationally and axially fasten the bone screw 12 to the sleeve 14. This would better restrict rotation of the bone screw 12.

As is apparent from FIGS. 3C and 3D, the fastening mechanism 48 has a first or unlocked position shown in dashed lines where the locking lever 44 is substantially parallel to the longitudinal direction. In the first or unlocked position, the sleeve 14 can move relative to the bone screw 12. Movement of the locking lever 44 from the first or unlocked position towards the second or locked position, shown in solid lines, will cause the cam or eccentrically mounted disc 42 to engage the bone screw 12, thereby rotationally and axially fastening the sleeve 14 to the bone screw 12. In order to not obstruct the operative site, the locking lever 44 is preferably removable so that it can be removed when the locking mechanism 48 is in the locked or unlocked positions.

As the cam or eccentrically mounted disc 42 engages the bone screw 12 when it is moved to the locking position, the cam or disc 42 grips the bone screw 12 and will frictionally forces the teeth 16 into the bone 6. Preferably, the sleeve 14 would be biased toward the bone 6 such that the teeth 16 engage the bone 6 when in the unlocked position. But the motion of moving the lever 44 to the locked position additionally biases the sleeve 14 towards the bone 6 by gripping and pulling up on the bone screw 12. When the lever 44 is moved to the unlocked position, the biasing force would be released.

Figure 3E:
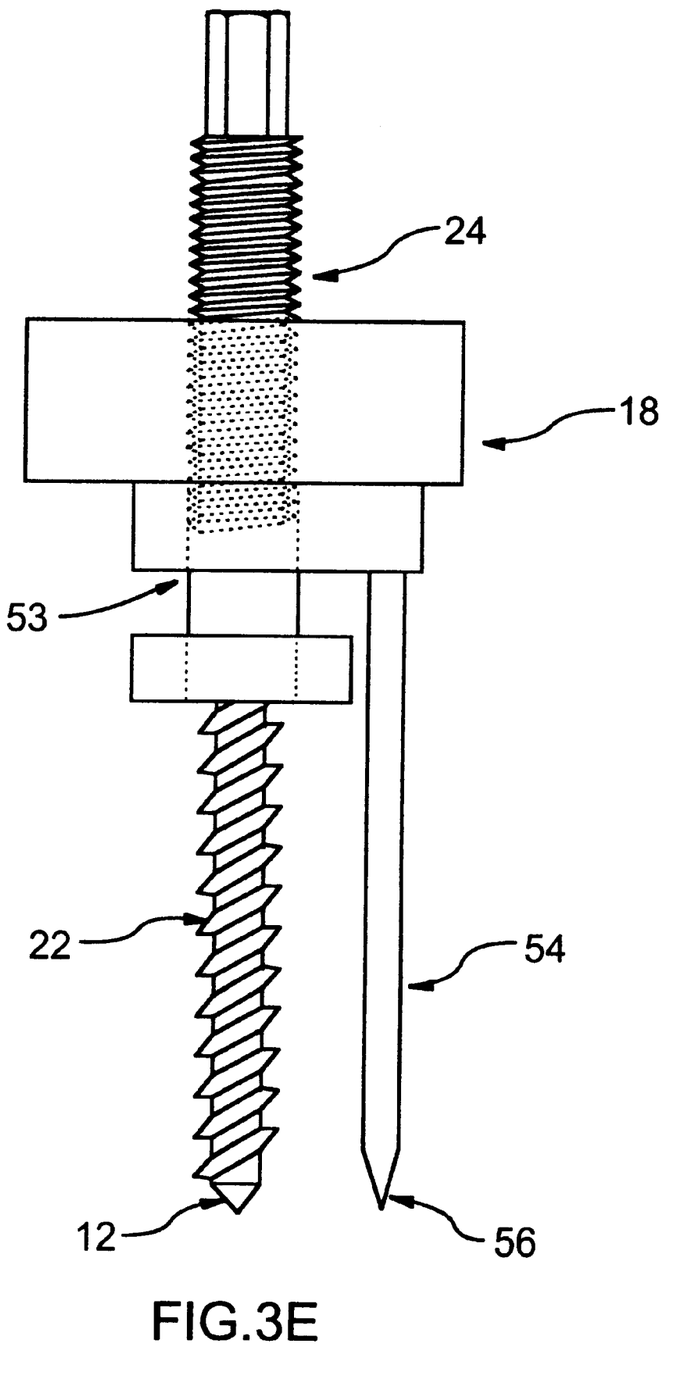
FIG. 3E shows a further embodiment of the present invention utilizing a pin.

FIG. 3E shows an embodiment of the present invention where a pin 54 is used as the rotation restricting member, rather than the sleeve 14. As shown in FIG. 3E, the pin has a hole or opening 53 which can axially receive the bone screw 12.

Rather than having serrated teeth, such as serrated teeth 16 shown in FIG. 1 to engage the surface of the bone 6, the pin 54 has a tip 56, which is preferably somewhat sharp. The tip 56 acts as the engaging element to engage the surface of the bone 6 to restrict rotation of the pin 54.

As shown in FIG. 3E, the fastening mechanism comprises a nut 18, similar to the nut 18 shown in FIG. 1. As shown in FIG. 3E, the nut 18 engages the second set of threads 24 on the bone screw 12. It is also understood that a nut, similar to the nut 25 shown in FIG. 3A, could be used to engage the first set of threads 22 in order to axially bias the pin 54 towards the bone 6 so that the tip 56 engages the bone surface.

Figure 3F:
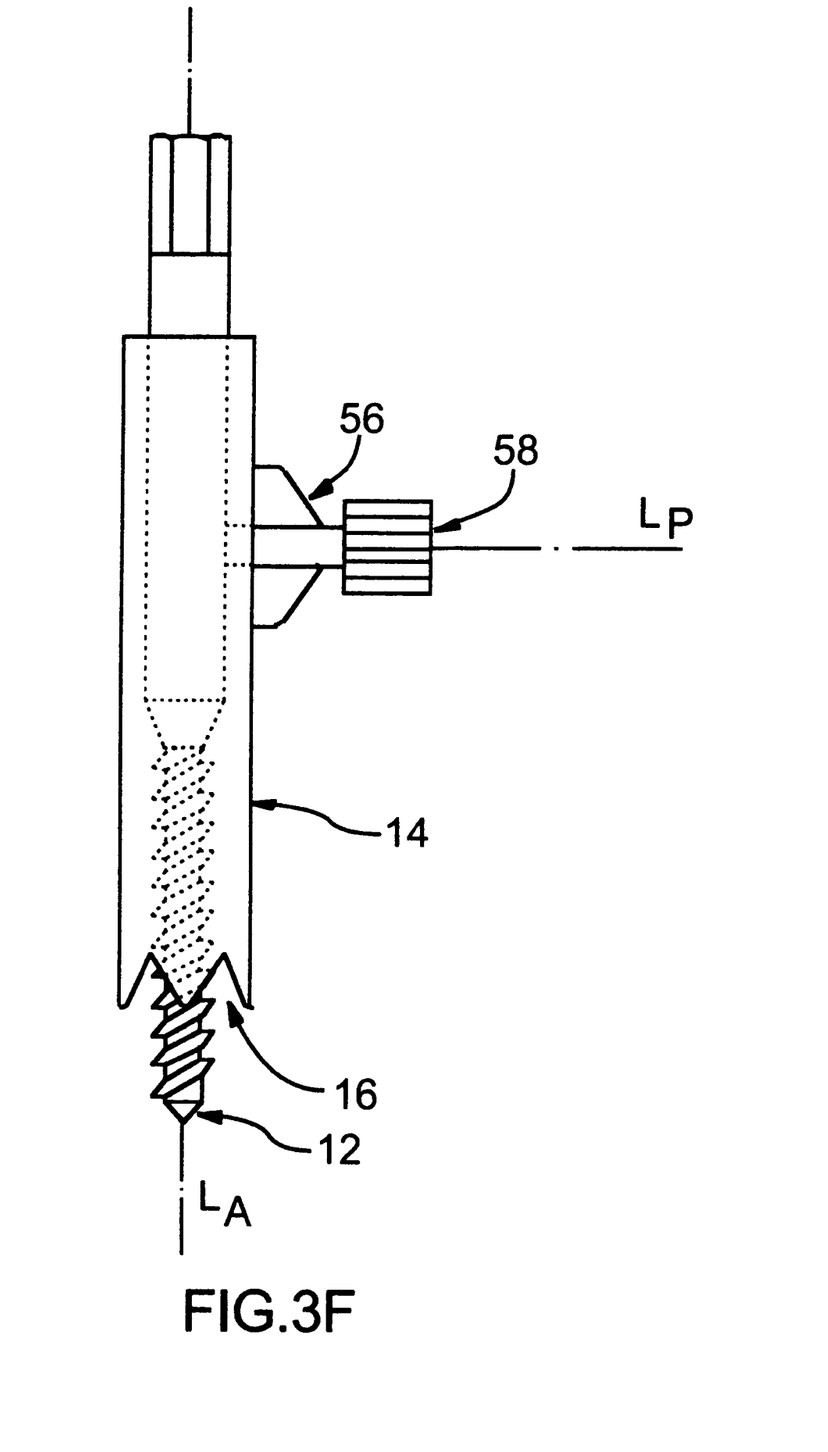
FIG. 3F illustrates a further embodiment of the present invention utilizing a thumb screw as the fastening mechanism.

FIG. 3F shows a still further embodiment of the present invention. In FIG. 3F, the sleeve 14 is similar to that shown in FIG. 1. However, the fastening mechanism shown in FIG. 3F comprises a screw 58 which comprises threads 56 connected to the sleeve 14. The threads 56 are located upon an axis $L_P$ which is substantially perpendicular to the longitudinal axis $L_A$. As the screw 58 is rotated about the substantially perpendicular axis $L_P$, the screw 58 engages the bone screw 12, thereby fastening the sleeve 14 to the bone screw 12.

One difference between the locking mechanism 58 and other locking mechanisms, such as the retainer 38 and the nut 18, is that the locking mechanism 58 does not, in and of itself, act to bias the sleeve 14 towards the surface of the bone 6. Rather, the locking mechanism 58 shown in FIG. 3F can fasten the sleeve 14 to the bone screw 12 after the sleeve 14 and serrated teeth 16 have been biased towards the bone 6, such as by means of a separate tool or hammer, or, a surgeon pressing the sleeve 14 towards the bone surface. After the sleeve 14 is biased towards the bone 6 and the serrated teeth 16 have been biased into engagement with the surface of the bone 6, the screw 58 is rotated so that the sleeve 14 is fastened to the bone screw 12. In either case, after the fastening mechanism 58 has fastened the sleeve 14 to the bone screw 12, it is understood that the serrated teeth 16 will be biased towards the bone 6 and will engage the surface of the bone 6 so as to fasten the sleeve 14 to the bone 6 and restrict rotation of the sleeve 14 about the longitudinal axis $L_A$.

Figure 3G:
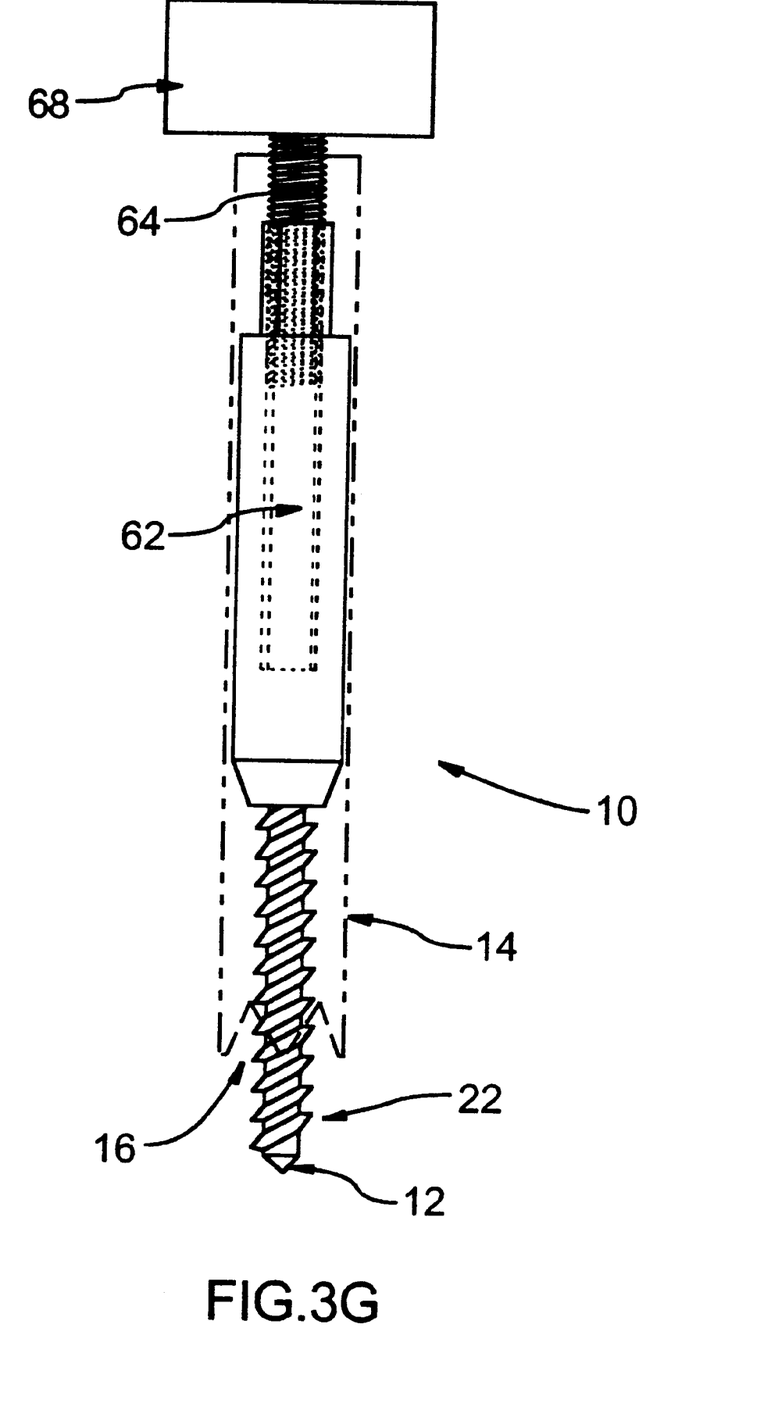
FIG. 3G illustrates a further embodiment of the present invention utilizing an internally threaded bone screw.

FIG. 3G shows a further embodiment of the present where the bone screw 12 has internal threads 62 and the fastening mechanism comprises a thumb-screw 68 having external threads 64. The external threads 64 engage the internal threads 62 to axially bias the sleeve 14 towards the bone 6, thereby biasing the serrated teeth 16 into engagement with the bone 6 and fastening the sleeve 14 to the bone screw 12.

It is understood that while the invention describes the object 8 being rotationally and axially secured to the bone 6, this does not necessarily mean that a large force applied to the object 8 or the bone screw 12 would not axially or rotationally displace the object 8 with respect to the bone 6. Rather, the device 10, and in particular the rotation restricting member, such as the sleeve 14, washer 25 or pin 54, axially and rotationally secures the object 8 to the bone 6 better than a bone screw 12 used alone. Nevertheless, the device according to the present invention would still be susceptible to displacement by large external forces.

It is also understood that while the present invention has been described in terms of a bone screw 12 to axially secure the device 10 and object 8 to the bone 6, it is understood that other types of axial supporting members could be used. For instance, a pin or nail (not shown), without necessarily having threads 22, could be used as an axial supporting member for axially securing the device 10 and the object 8 to the bone 6. In addition, bone screws which do not have coarse threads could also be used, such as for insertion in a drilled and tapped hole. Accordingly, it is understood that the present invention is not necessarily restricted to use of a bone screw 12, but rather encompasses other types of axial supporting members for axially securing the device 10 and object 8 to the bone 6.

It is also understood that while the present invention has been described in terms of a rotation restricting member, such as a sleeve 14, a washer 25 or pin 54, the present invention is not limited to these types of rotation restricting members. Rather, the present invention encompasses all types of rotation restricting elements that can be biased towards the bone 6 after it is fastened to an axial supporting member, such as a bone screw 12, such that an engaging element, including serrated teeth 14, 23, can engage the bone 6 to restrict rotation of the rotation restricting member.

It is further understood that reference to a bone 6 is not restricted to a particular bone. Rather, subject to the discretion of a surgeon, the present invention could be used in association with any bone or bone fragment within a human being, an animal or a cadaver.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

The embodiments of the invention in which an exclusive property or privilege is claimed are defined as follows:

1. A device for releasably securing an object to a bone, said device comprising:
   a rotation restricting member having an engaging element which engages the bone to restrict rotation of the member;
   a fastening mechanism for fastening the rotation restricting member to a bone screw engaging the bone, said fastening mechanism comprising a retainer fixed to the bone screw, said retainer having a stop which engages the rotation restricting member such that insertion of the bone screw to a predetermined depth in the bone biases the engaging element to engage the bone, thereby restricting rotation of the rotation restricting member;

a clamp for releasably securing the object to the rotation restricting member or the bone screw;

wherein after the fastening mechanism has fastened the rotation restricting member to the bone screw, the rotation restricting element is biased towards the bone such that the engaging element engages the bone to restrict rotation of the member; and wherein releasably securing the object to the clamp axially and rotationally secures the object to the bone.

2. The device as claimed in claim 1 wherein the rotation restricting member comprises a sleeve which axially receives the bone screw; and wherein the engaging element comprises serrated teeth which can engage a surface of the bone to restrict rotation of the sleeve about the bone screw.

3. The device as claimed in claim 2 wherein the fastening mechanism comprises a nut that engages the bone screw;

and wherein the nut engages the bone screw and the sleeve such that the sleeve is axially biased towards the bone, thereby fastening the sleeve to the bone screw and biasing the serrated teeth towards the bone.

4. The device as claimed in claim 3 wherein the bone screw has a first set of threads that engage the bone and a second set of threads which the nut engages.

5. The device as claimed in claim 3 wherein the bone screw has a first set of threads that engage the bone and the nut engages the first set of threads; and wherein the clamp secures the object to the sleeve.

6. The device as claimed in claim 2 wherein the fastening mechanism axially biases the sleeve towards the bone to bias the serrated teeth into engagement with the bone and to fasten the sleeve to the bone screw.

7. The device as claimed in claim 3 wherein the stop engages the sleeve such that insertion of the bone screw to a predetermined depth in the bone biases the serrated teeth towards the bone to restrict rotation of the sleeve.

8. The device as claimed in claim 1 wherein the rotation restricting member comprises a pin; and wherein the engaging element comprises a tip of the pin which can engage the bone to restrict rotation of the sleeve about the bone screw.

9. The device as claimed in claim 1 wherein the rotation restricting member comprises a washer having an opening which axially receives the bone screw; and wherein the engaging element comprises serrated teeth which can engage the bone to restrict rotation of the washer about a longitudinal axis of the bone screw.

10. A device for releasably securing an object to a bone, said device comprising:

a clamp releasably securable to the object;

an axial supporting member for axially securing the device to the bone;

a rotation restricting member which, while engaging the bone, restricts rotation of the device;

a fastening mechanism for fastening the axial supporting member with respect to the rotation restricting member, said fastening mechanism comprising a retainer fixed to the bone screw, said retainer having a stop which engages the rotation restricting member such that insertion of the bone screw to a predetermined depth in the bone causes the rotation restricting member to engage the bone and strict rotation of the device;

wherein the fastening mechanism fastens the axial supporting member to the rotation restricting member while the axial supporting member and the rotation restricting member are engaging the bone; and wherein objects can be releasably secured to the clamp, after the fastening mechanism has fastened the axial supporting member with respect to the rotational supporting member, to axially and rotationally secure the objects to the bone.

11. The device as claimed in claim 10 wherein the axial supporting member comprises a bone screw with a first set of threads that engage the bone.

12. The device as claimed in claim 11 wherein the rotation restricting member comprises a washer having an opening which receives the bone screw; and wherein the washer comprises serrated teeth which can engage the bone to restrict rotation of the washer.

13. The device as claimed in claim 12 wherein the fastening mechanism comprises a nut which engages the first set of threads; and wherein rotation of the nut causes the washer to move towards the bone such that the teeth engage the bone and the nut fastens the washer to the bone screw.

14. The device as defined in claim 10 wherein the rotation restricting member comprises a sleeve which axially receives said axial supporting member; and wherein the sleeve comprises serrated teeth which can engage the bone to restrict rotation of the sleeve about the axial supporting member.

15. The device as defined in claim 14 wherein the fastening mechanism comprises a nut that engages a set of threads on the axial supporting member;

wherein rotation of the nut about the set of threads causes the sleeve to move towards the bone such that the serrated teeth engage the bone and the nut fastens the sleeve to the axial supporting member.

16. A device to restrict rotational displacement of a bone screw, said device comprising:

a rotation restricting member having an engaging element which engages the bone to restrict rotation of the rotation restricting member;

a fastening mechanism for fastening the rotation restricting member to the bone screw, said fastening mechanism comprising a retainer fixed to the bone screw, said retainer having a which engages the rotation restricting member such that insertion of the bone screw to a predetermined depth in the bone biases the engaging element to engage the bone, thereby restricting rotation of the rotation restricting member;

wherein the fastening mechanism fastens the rotation restricting member to the bone screw while the engaging element is engaging the bone, thereby preventing rotational displacement of the bone screw.

17. The device as claimed in claim 16 wherein the rotation restricting member comprises a sleeve which axially receives the bone screw; and wherein the engaging element comprises serrated teeth which can engage a surface of the bone to restrict rotation of the sleeve about a longitudinal axis of the bone screw.

18. The device as claimed in claim 16 wherein the fastening mechanism rotationally and axially fastens the bone screw to the rotation restricting element.

19. The device as claimed in claim 16 further comprising a clamp for releasably securing an object to the sleeve or the bone screw thereby axially and rotationally securing the object to the bone.

20. A device for releasably securing an object to a bone, said device comprising:
- a rotation restricting member having an engaging element which engages the bone to restrict rotation of the member,
- a bone screw for engaging the bone;
- a biasing member for axially biasing the rotation restricting element with respect to the bone screw, said biasing member comprising a retainer fixed to the bone screw, said retainer having a stop which engages the rotation restricting member;
- wherein inserting the bone screw to a predetermined depth causes the biasing member to axially bias the rotation restricting member with respect the bone screw such that the engaging element engages the bone to restrict rotation of the member; and
- wherein releasably securing the object to the rotation restricting member axially and rotationally secures the object to the bone.

21. A method of releasably securing an object to a bone, said method comprising the steps of:
- fixing a biasing member to a longitudinal position on a bone screw, said bone screw having a bone engaging end;
- axially inserting a rotation restricting member onto the bone engaging end of the bone screw, said rotation restricting member having an engaging element which engages the bone to restrict rotation of the rotation restricting member;
- driving the bone engaging element of the bone screw into the bone until the biasing member biases the engaging element of the rotation restricting member into the bone;
- clamping the object to the rotation restricting element or the bone screw.

* * * * *